(12) United States Patent
Oki et al.

(10) Patent No.: US 9,683,936 B2
(45) Date of Patent: Jun. 20, 2017

(54) LIGHT-INDUCED FLUORESCENT MEASURING DEVICE

(71) Applicants: USHIO DENKI KABUSHIKI KAISHA, Tokyo (JP); KYUSHU UNIVERSITY, NATIONAL UNIVERSITY CORPORATION, Fukuoka (JP)

(72) Inventors: Yuji Oki, Fukuoka (JP); Hiroaki Yoshioka, Fukuoka (JP); Kinichi Morita, Tokyo (JP)

(73) Assignees: USHIO DENKI KABUSHIKI KAISHA, Tokyo (JP); KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 107 days.

(21) Appl. No.: 14/417,905

(22) PCT Filed: Jul. 5, 2013

(86) PCT No.: PCT/JP2013/068477
§ 371 (c)(1),
(2) Date: Jan. 28, 2015

(87) PCT Pub. No.: WO2014/021055
PCT Pub. Date: Feb. 6, 2014

(65) Prior Publication Data
US 2015/0153279 A1 Jun. 4, 2015

(30) Foreign Application Priority Data
Aug. 2, 2012 (JP) ................................. 2012-171825

(51) Int. Cl.
*G01N 21/64* (2006.01)
*G01N 33/533* (2006.01)
(Continued)

(52) U.S. Cl.
CPC ....... *G01N 21/645* (2013.01); *G01N 21/6402* (2013.01); *G01N 27/44721* (2013.01);
(Continued)

(58) Field of Classification Search
CPC .................................................... G01N 21/645
See application file for complete search history.

(56) References Cited

U.S. PATENT DOCUMENTS 4,919,513 A * 4/1990 Nakakuki ............... B29C 39/18
385/127
5,006,210 A * 4/1991 Yeung .............. G01N 27/44721
204/452

(Continued)

FOREIGN PATENT DOCUMENTS

JP H10-62349 A 3/1998
JP H11-271217 A 10/1999
(Continued)

OTHER PUBLICATIONS

International Search Report; PCT/JP2013/068477; Oct. 8, 2013.

*Primary Examiner* — David Porta
*Assistant Examiner* — Jeremy S Valentiner
(74) *Attorney, Agent, or Firm* — Studebaker & Brackett PC

(57) ABSTRACT

A laser light source for emitting excitation light, a sample case, a photomultiplier tube, a fluorescence collecting optical system and so forth are embedded in a resin material that is transparent to the excitation light and the light including fluorescence emitted from a sample. The resin material is provided in at least part of a light path that guides the fluorescence in the fluorescence collecting optical system, and this resin forms a housing that holds the laser light source, the fluorescence collecting optical system, the photomultiplier and so forth. A pigment having wavelength characteristics for absorbing the excitation light, Raman (Continued)

light generated from the resin, and so forth is contained substantially in a uniform manner in a resin region that surrounds the light path through which the excitation light and the light including the fluorescence pass.

18 Claims, 6 Drawing Sheets

(51) Int. Cl.
  *G01N 27/447* (2006.01)
  *G01N 33/00* (2006.01)
(52) U.S. Cl.
  CPC ..... *G01N 33/0057* (2013.01); *G01N 2201/02* (2013.01); *G01N 2201/0221* (2013.01); *G01N 2201/06113* (2013.01)

(56) References Cited

U.S. PATENT DOCUMENTS

| | | | |
|---|---|---|---|
| 5,039,490 A * | 8/1991 | Marsoner | G01N 21/255 250/216 |
| 5,360,739 A * | 11/1994 | Fan | G01N 1/30 435/29 |
| 6,867,420 B2 | 3/2005 | Mathies et al. | |
| 7,738,099 B2 | 6/2010 | Morrell et al. | |
| 8,031,336 B2 | 10/2011 | Shibayama et al. | |
| 8,373,851 B2 | 2/2013 | Hoenes et al. | |
| 8,477,305 B2 | 7/2013 | Shibayama et al. | |
| 8,477,306 B2 | 7/2013 | Shibayama et al. | |
| 2003/0222223 A1 | 12/2003 | Kamei et al. | |
| 2004/0120667 A1* | 6/2004 | Aylward | G02B 6/08 385/115 |
| 2008/0277606 A1* | 11/2008 | Wang | B01L 3/5027 250/581 |
| 2010/0108910 A1 | 5/2010 | Morrell et al. | |
| 2012/0270338 A1 | 10/2012 | Ueda et al. | |
| 2013/0003043 A1 | 1/2013 | Hoenes et al. | |
| 2014/0030800 A1* | 1/2014 | Moses | G01N 21/64 435/288.7 |

FOREIGN PATENT DOCUMENTS

| | | |
|---|---|---|
| JP | 2000-241428 A | 9/2000 |
| JP | 2005-535871 A | 11/2005 |
| JP | 2008-215851 A | 9/2008 |
| JP | 2008-292220 A | 12/2008 |
| JP | 2009-501907 A | 1/2009 |
| JP | 2012-208134 A | 10/2012 |
| JP | 2013-518270 A | 5/2013 |
| WO | 03/102554 A1 | 12/2003 |
| WO | 2007/011854 A2 | 1/2007 |
| WO | 2007/011854 A3 | 1/2007 |
| WO | 2011/061944 A1 | 5/2011 |

* cited by examiner

LIGHT-INDUCED FLUORESCENT MEASURING DEVICE

TECHNICAL FIELD

The present invention relates to a light-induced fluorescent measuring device that is compact, easy to carry, has a simple structure and carries out high speed measuring at high performances.

BACKGROUND ART

In general, sensitivity of emission spectrometry (emission analysis) that uses luminous phenomena of substances, materials, molecules and atoms is very high. One of known analyzing methods that use such emission is an LIF (laser-induced fluorescence) method that uses a laser beam.

The LIF method takes advantage of resonant transition of an atom and/or a molecule, which is a target to be measured. The LIF method irradiates the measurement target (atom or molecule) with the laser beam that matches an excitation level (laser beam having a tuned wavelength) to excite the measurement target. The light emission (fluorescence) takes place from the measurement target upon such excitation. The LIF method measures the light emission (fluorescence).

The density (concentration) of the measurement target is calculated from the intensity of the fluorescence, and the temperature of the measurement target is calculated from a spectral distribution of the fluorescence.

The LIF method is employed in various technical fields. In an environment technology, for example, the LIF method may be used to measure the concentration of NOx (nitrogen oxide) in the air, as disclosed in Patent Literature 1 (will be mentioned below). In metallurgy, the LIF method may be used to measure concentrations of chemical elements in a molten metal inside a metal refining furnace, as disclosed in Patent Literature 2 (will be mentioned below).

The LIF method is particularly employed in a wide range of bioanalysis in the life science technology. The florescence is useful in the bioanalysis. By detecting fluorescence radiated (emitted) from a sample S, which is irradiated with the laser beam, it is possible to extract information such as a biochemical composition of the sample S, physical characteristics of the sample S, chemical characteristics of the sample S, spectral characteristics of the sample S, a structure of a biochemical sample and a structure of an organism sample (biological sample). The duration of fluorescence (how long the fluorescence lasts) is usually in the order of ps (picosecond) to ns (nanosecond). Thus, use of the LIF method enables the measurement with the time resolution in the order of μs (microsecond), which is the in vivo action time of the biological sample.

An example of the LIF method used in the life science technology is found in Patent Literature 3 (will be mentioned below). Patent Literature 3 discloses an early warning system to terrorism in a city that uses a biological weapon such as anthrax. This early warning system employs the LIF method to detect the biological weapon.

Patent Literature 4 (will be mentioned below) discloses a measuring apparatus that causes electrophoresis of a biological sample, which is labelled (marked) with fluorescence, in a microchip and analyze the biological sample with the LIF method. Patent Literature 5 (will be mentioned below) discloses a kit that has an antibody light chain variable domain (region) polypeptide and an antibody heavy chain variable domain polypeptide, with one of the antibody light chain variable domain polypeptide and the antibody heavy chain variable domain polypeptide being labelled with a fluorescent dye. Patent Literature 5 also discloses detection of fluorescence intensity of the fluorescent pigment to measure the concentration (density) of an antigen that reacts with the kit. Patent Literature 5 shows an example in which the detection of the fluorescence intensity uses the LIF method. Patent Literature 6 (will be mentioned below) discloses an antigen measuring device that uses the LIF method.

FIG. 6 of the accompanying drawings illustrates a configuration of an antigen measuring device of Patent Literature 6 that uses the LIF method. Although the detail is not described, the measurement is carried out, for example, in the following manner. A capillary column 101 and an electrode 103a are inserted in a buffer vial 102 that holds a sample S containing an antibody, and another capillary column 101 and another electrode 103b are inserted in another buffer vial 102 that holds a sample S containing an antibody.

An antigen is introduced to the sample S, and an antibody-antigen reaction takes place in the sample. As an electric power is supplied from a high voltage source 110, the electrophoresis causes an antibody-antigen compound and the antibody to separate from the sample. Thus, the antibody-antigen compound and the antibody move through the capillary column(s) 101. In the meantime, the electric power supply is stopped, and the antibody-antigen compound and/or the antibody undergoes an enzyme reaction. Upon resuming the electric power supply, the electrophoresis causes the antibody-antigen compound and the antibody, which have finished the enzyme reaction, to move to a measuring position to which the laser beam 11 emitted from a laser device 105 is reflected by a mirror 106 and condensed by a condensing lens 104. The antibody-antigen compound and the antibody, which have finished the enzyme reaction and reached the measuring position, are irradiated with the laser beam 111 and become fluorescent (emit fluorescence).

The fluorescence passes through the mirror 106, which is designed to reflect the laser beam 111 but transmits the fluorescent light (fluorescence), and is reflected by another mirror 107, which is designed to reflect the fluorescence. Then, the fluorescence is incident to a photomultiplier tube 109 via an optical filter 108. In this manner, the intensity of the fluorescence is measured.

The optical filter 108 blocks the scattered light of the laser beam, which is excitation light, and transmits the fluorescence only. The optical filter 108 has a capability of selectively transmitting the fluorescence. The optical filter 108 prevents the scattered light of the laser beam from entering the photomultiplier tube 109. The antibody-antigen compound and the antibody, which have undergone the enzyme reaction, have different moving speeds during the electrophoresis. Thus, the fluorescence from the antibody-antigen compound that has undergone the enzyme reaction arrives at the photomultiplier tube 109 at a different timing from the fluorescence from the antibody which has undergone the enzyme reaction.

LISTING OF REFERENCES

Patent Literatures

PATENT LITERATURE 1: Japanese Patent Application Laid-Open Publication No. 2008-292220

PATENT LITERATURE 2: Japanese Patent Application Laid-Open Publication No. 2008-215851

PATENT LITERATURE 3: Japanese Patent Application Laid-Open Publication No. 2009-501907

PATENT LITERATURE 4: Japanese Patent Application Laid-Open Publication No. 2005-535871

PATENT LITERATURE 5: PCT International Publication No. WO 2011/061944 A1

PATENT LITERATURE 6: Japanese Patent Application Laid-Open Publication No. 2000-241428

SUMMARY OF THE INVENTION

Problems to be Solved by the Invention

In the life science technology of recent years, there is an increasing demand for a POCT (point of care testing). There is a greater demand for a compact and portable measuring device that can be used for analysis at a desired site, can finish the testing in a short time, and provide evaluation and analysis at a high accuracy. Thus, there is a demand for application of a measuring device that uses the LIF method (referred to as "LIF measuring device" hereinafter) in the above-mentioned use.

As already shown in FIG. 6, the LIF measuring device includes the fluorescence measuring unit (e.g., photomultiplier tube), the optical filter(s), the optical lens(es), the laser light source and other components. In order to provide a compact and portable LIF measuring device, a separating system that relies on the electrophoresis may be fabricated in the form of microchip, for size reduction. In this configuration, the distance between the laser light source and the fluorescence measuring device is naturally reduced. Thus, influences of the reflection and scattering of the laser beam, which is the excitation light directed to the measurement target, inside the LIF measuring device are not negligible.

Specifically, because the laser beam passes through the light-permeable microchip, which has the optical elements (e.g., the condensing lens and the optical filter) and the measurement target therein, and other components, the reflection and scattering of the laser beam occur inside the LIF measuring device. As the distance between the laser light source 1 and the fluorescence measuring device is reduced, the scattered light and the reflected light of the laser beam arrive at the fluorescence measuring unit at an extremely high probability. Upon the size reduction of the LIF measuring device, the distance between a housing of the LIF measuring device (not shown in the example of FIG. 6) and the laser light source 1 decreases, and the distance between the housing of the LIF measuring device and the fluorescence measuring unit decreases. Thus, influences of the reflection and scattering of the laser beam inside the LIF measuring device housing are not negligible.

In general, the intensity of the laser beam, which is the excitation light, is significantly greater than the intensity of the fluorescence generated from the measurement target. Therefore, when the reflected light and/or the scattered light of the laser beam enters the fluorescence measuring unit, the reflected light and the scattered light exert a serious influence on the fluorescence detection sensitivity of the fluorescence measuring unit, even though the intensity of the reflected light and the scattered light of the laser beam is very small compared to the intensity of the original laser beam.

In order to eliminate such influence of the reflected light and the scattered light, a plurality of optical filters are used, for example. This makes the optical system of the LIF measuring device complicated. Optical components that constitute such complicated optical system are held by an optical component holder inside the LIF measuring device. If the LIF measuring device is a compact and portable device, however, there is a possibility that the alignment of the optical system may be lost (may not be maintained) due to vibrations during transport and carriage, or unexpected impacts generated upon collisions to a certain structure.

When the alignment of the optical system is lost, it is then necessary to adjust (recover) the alignment of the optical system in the LIF measuring device. However, as described above, the optical system built inside the LIF measuring device is complicated. Therefore, a high skill is required to a worker to adjust the alignment.

The POCT (point of care testing) is used, for example, in the inspection on an ambulance, the self-diagnosis by a patient at home, and the outdoor test for proscribed drugs. Not all the persons who carry out the POCT have a skill to adjust the alignment of the optical system in the LIF measuring device.

Therefore, the holder for the optical components has to have a rigid and large structure to suppress or avoid the misalignment of the optical system upon subjected to the vibrations and impacts.

In order to minimize the influence of the scattered light and the reflected light of the laser beam, the optical system of the LIF measuring device includes a large number of optical components, as described above. Accordingly, the holder for the optical components inevitably has a large and complicated structure, and the optical system including the optical components inevitably has a large and complicated structure.

In short, the conventional technology is very difficult to provide a LIF measuring device that meets the demand for the POCT. Specifically, the conventional technology is very difficult to provide a LIF measuring device that is compact, portable, transportable, and can perform the measurement at high speed and at high accuracy.

The present invention is developed in consideration of the above-described facts. One object of the present invention is to provide a light-induced fluorescence measuring device that can suppress the misalignment of the optical system in the measuring device even if the measuring device is subjected to vibrations during carriage and transport and impacts upon an unexpected collision to a certain structure. One object of the present invention is to provide a light-induced fluorescence measuring device that has a relatively simple optical system to reduce the incidence of the reflected light and the scarred light of the excitation light into the fluorescence measuring unit. One object of the present invention is to provide a light-induced fluorescence measuring device that can meet the demand for the point of care testing, i.e., a light-induced fluorescence measuring device that is compact, easy to carry, and enables the simple and fast measurement with high-performances.

Solution to the Problems

The present invention achieves the above-described objects in the following manner.

(1) According to a first aspect of the present invention, there is provided a light-induced fluorescence measuring device that includes: a solid light source; a sample holding member configured to hold a sample; a fluorescence measuring unit configured to detect fluorescence emitted (radiated) from the sample held by the sample holding member; and a fluorescence collecting optical system configured to collect the fluorescence emitted from the sample and optically guide the fluorescence to the fluorescence measuring unit. The sample holding member is permeable (transparent) to light (excitation light) emitted from the solid light source and the fluorescence radiated from the sample. The light emitted from the solid light source is excitation light. The solid light source, the sample holding member, the fluorescence measuring unit, and the fluorescence collecting optical system are embedded in a resin material. The resin material is permeable to the excitation light emitted from the solid light source and light including the fluorescence radiated from the sample. At least part of an optical path of the fluorescence collecting optical system for optically guiding the fluorescence is filled with the resin material. The resin material forms a housing for holding the sample holding member, the fluorescence measuring unit and the fluorescence collecting optical system.

That part of the resin material, which surrounds the optical path for the excitation light and the light including the fluorescence radiated from the sample, contains in a substantially uniform manner a pigment that has a wavelength characteristic to absorb the excitation light, intrinsic fluorescence generated upon irradiating the sample holding member with the excitation light, and Raman light generated from the resin material when the excitation light proceeds in the resin material. An amount of the pigment to be contained in the resin material is set to a value that completely absorbs light, which is generated in a space including the optical path for the excitation light and the light including the fluorescence radiated from the sample and which proceeds out of the optical path.

(2) In the light-induced fluorescence measuring device according to the first aspect of the present invention, the fluorescence collecting optical system may have, at least, a lens, a notch filter, and a color glass filter.

(3) In the light-induced fluorescence measuring device according to the above-described (2), the fluorescence collecting optical system may have two lenses, a second space defined between the two lenses may be a hollow space, which is not filled with the resin material, two interfaces between the hollow space and the resin material may have lens shapes respectively such that part of the resin material may form the two lenses.

(4) In the light-induced fluorescence measuring device according to the above-described (2) or (3), the fluorescence collecting optical system may have, from an incident side of the excitation light and the light including the fluorescence radiated from the sample, a first notch filter configured to reflect light having a wavelength of the excitation light emitted from the solid light source, a first lens configured to convert the excitation light and the light including the fluorescence radiated from the sample into parallel light, a second notch filter configured to reflect the light having the wavelength of the excitation light, a first color glass filter configured to absorb light other than the fluorescence radiated from the sample, a second lens configured to condense (concentrate) the light including the fluorescence, and an aperture formed on an optical axis of the second lens and situated in the vicinity of a fluorescence condensing position.

(5) In the light-induced fluorescence measuring device according to the above-described (1), (2), (3) or (4), the sample held by the sample holding member may include a kit that may have an antibody light chain variable domain polypeptide and an antibody heavy chain variable domain polypeptide, and one of the antibody light chain variable domain polypeptide and the antibody heavy chain variable domain polypeptide may be labelled with a fluorescent dye.

Advantageous Effects of the Invention

The present invention may provide the following advantages.

(1) The solid light source, the sample holding member for holding a measurement sample, the fluorescence collecting optical system having lenses, optical filters and other components, and the fluorescence measuring unit are embedded in the resin material that is permeable (transparent) to the excitation light emitted from the solid light source and the light including the fluorescence radiated from the sample. Therefore, even if vibrations and/or impacts are applied to the light-induced fluorescence measuring device, the positional displacements of the optical components do not take place easily. As a result, the alignment disorder of the fluorescence collecting optical system is suppressed.

Also, the contact (fitting) between the resin material and the optical components is good, and therefore undesired light reflection and scattering, which would otherwise be caused by an air present at the contact area between the resin material and the optical components, hardly occur.

(2) That part of the resin material, which surrounds the optical path for the excitation light emitted from the solid light source and the light including the fluorescence radiated from the sample, contains a pigment that has a wavelength characteristic to absorb the excitation light, intrinsic fluorescence generated upon irradiating the sample holding member with the excitation light, Raman light generated from the resin material, and other light. An amount of the pigment to be contained is set to a value that completely absorbs light, which is generated in a space including the optical path for the excitation light and the light including the fluorescence radiated from the sample and which proceeds out of the optical path. Therefore, the excitation light and the fluorescence, which is the light to be measured, are not released out of the fluorescence measuring device. Also, the outside light does not enter the fluorescence collecting optical system and other components, and the measurement is conducted at high accuracy.

In particular, because the resin that contains the pigment (pigment-containing resin) is made from the same material as the transparent resin that embeds the solid light source, the sample holding member, the fluorescence collecting optical system and other components, the pigment-containing resin has the same refractive index as the transparent resin. Accordingly, there is no refractive index boundary between the area occupied by the transparent resin and the area occupied by the pigment-containing resin.

Thus, when the light that passes through the area occupied by the transparent resin is incident to the area occupied by the pigment-containing resin, the reflection and scattering of the light at the interface between the transparent resin and the pigment-containing resin occur in a limited manner. Even if the excitation light, the reflected light of the excitation light, the scattered light of the excitation light, and/or other light is incident to the area occupied by the pigment-containing resin, all of such light is absorbed by the pigment contained in the pigment-containing resin. Thus, the stray light of the reflected light of the excitation light, the scattered light of the excitation light and other light hardly returns to the laser irradiation space and the space for the fluorescence collecting optical system.

When equipment designed with general specifications uses a laser beam, it is important for the equipment to be able to ensure safety for a human body (particularly the safety for human eyes). When the fluorescence measuring device of the present invention is used, risks against the safety for the human body are significantly reduced because of the three points: (i) normally the light does not leak to outside; (ii) there is no risk of leakage of the light to outside due to breakage, unlike a spectroscopic optical system made from glass; and (iii) because most of the light guiding area is the solid, the light leakage is difficult to occur when a person peeks into the fluorescence measuring device and when a mirror is inserted into the fluorescence measuring device.

Also, complicated multi-reflection (multipath reflection) of the stray light hardly takes place, and therefore the fluorescence collecting optical system does not have to cope with the complicated multi-reflection. Thus, the structure of the fluorescence collecting optical system is simplified. As a result, it is possible to make the laser-induced fluorescence measuring device of the present invention compact.

(3) The second space defined between the two opposite lenses of the fluorescence collecting optical system may be a hollow space, which is not filled with the transparent (permeable) resin material. The two interfaces between the hollow space and the resin material may be shaped like lens respectively. Thus, part of the resin material may form the two lenses. Separate lenses such as glass lenses are not necessary, and it is possible to reduce the number of parts (components).

(4) That part of the resin material, which surrounds the optical path for the excitation light and the light including the fluorescence radiated from the sample, may be the pigment-containing resin, and the fluorescence collecting optical system may have a first notch filter configured to reflect light having a wavelength of the excitation light emitted from the solid light source, a first lens configured to convert the excitation light and the light including the fluorescence radiated from the sample into parallel light, a second notch filter configured to reflect the light having the wavelength of the excitation light, a first color glass filter configured to absorb light other than the fluorescence radiated from the sample, a second lens configured to condense (concentrate) the light including the fluorescence, and an aperture provided in the vicinity of a fluorescence condensing position. Therefore, it is possible to efficiently condense the measurement target fluorescence only, and guide it to the fluorescence measuring unit. It is also possible to substantially absorb light other than the measurement target fluorescence while the light proceeds in the optical path such that light other than the measurement target fluorescence is prevented from arriving at the fluorescence measuring unit.

(5) The sample held by the sample holding member may include a kit that has an antibody light chain variable domain polypeptide and an antibody heavy chain variable domain polypeptide, with one of the antibody light chain variable domain polypeptide and the antibody heavy chain variable domain polypeptide being labelled with a fluorescent dye. An antigen is injected into the antibody labelled by the fluorescent material to make a mixture liquid, and the mixture liquid is irradiated with the excitation light to generate and measure the fluorescence. Then, it is possible to easily measure the binding condition between the antigen and the antibody.

DETAILED DESCRIPTION OF EMBODIMENTS OF THE INVENTION

Figure 1:
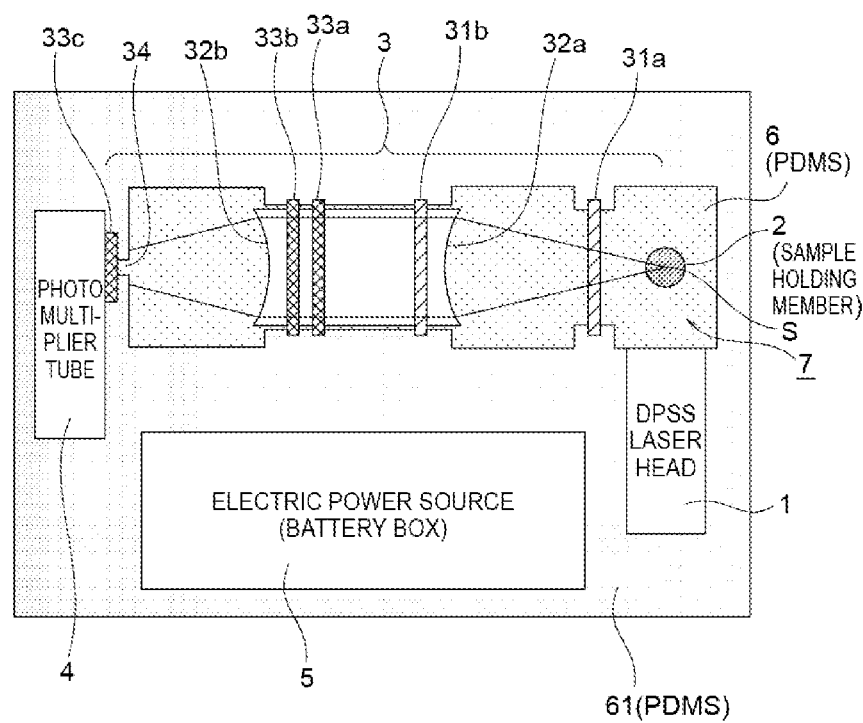
FIG. 1 illustrates an overall structure of a light-induced fluorescence measuring device according to one embodiment of the present invention.

FIG. 1 illustrates an overall structure of a light-induced fluorescence measuring device according to one embodiment of the present invention. In the embodiment shown in FIG. 1, the laser-induced fluorescence measuring device has a rectangular parallelepiped shape. Side views of the measuring devices are omitted. FIG. 1 is a cross-sectional view taken along a plane which is substantially parallel to a top face of the rectangular parallelepiped.

As shown in FIG. 1, the light-induced fluorescence measuring device of this embodiment includes a solid light source (e.g., laser light source 1), a sample holding member (sample casing 2) to hold a sample S to be measured, a fluorescence collecting optical system 3 having lenses, optical filters and the like, and a fluorescence measuring unit (e.g., photomultiplier tube 4). The solid light source 1, the sample holding member 2, the fluorescence collecting optical system 3, and the fluorescence measuring unit 4 are embedded in resin 6. An electric power source 5 is also embedded in the resin 6 to feed an electric power to the solid light source and the fluorescence measuring unit if necessary. The resin 6 serves as a housing for holding the sample holding member, the fluorescence measuring unit, the fluorescence collecting optical system, and other components and elements.

The solid light source may be a laser light source 1 (e.g., semiconductor laser, laser diode, or DPSS (diode-pumped solid state) laser). Alternatively, the solid light source may include one or more LEDs (light emitting diode) or other suitable elements. In the following description, the solid light source is a laser light source, and the light-induced fluorescence measuring unit of the present invention is a laser-induced fluorescence measuring unit. In FIG. 1, the DPSS laser is driven by a battery disposed in a battery box of the electric power source 5. Only a laser head of the DPSS laser is located at a prescribed position to irradiate the sample S with a laser beam L.

The resin 6 is transparent (permeable) to the wavelength of the excitation light (sometimes referred to as "laser beam L" hereinafter) that is emitted toward the sample from the laser light source 1 and the wavelength of light including fluorescence emitted (radiated) from the sample S, which is irradiated with the excitation light.

At least part of space (laser irradiation space 7) for holding the sample S, which is irradiated with the laser beam L from the laser light source 1, is filled with the resin 6. Also, at least part of space in the fluorescence collecting optical system 3 that defines an optical path to guide the fluorescence, which is radiated (emitted) from the sample S, to the photomultiplier tube 4 (i.e., fluorescence measuring unit) is filled with the resin 6. The resin 6 is permeable (transparent) to the above-mentioned wavelengths. The resin 6 may be silicone, acryl, polycarbonate, COC (cyclic olefin copolymer), COP (cyclic olefin polymer), or the like. In the embodiment that will be described below, silicone is used as the resin 6.

In the fluorescence collecting optical system 3 shown in FIG. 1, there are disposed a first notch filter 31a, a first lens 32a, a second notch filter 31b, a first color glass filter 33a, a second color glass filter 33b, a second lens 32b, an aperture 34 and a third color glass filter 33c. The space between the lenses 32a and 32b is not filled with the resin 6, but filled with the air and sealed. This space is a vacant space. The remaining space in the fluorescence collecting optical system 3 is filled with the permeable silicone resin 6.

It should be noted that the entire laser irradiation space 7 and the entire space in the fluorescence collecting optical system 3 may be filled with the silicone resin 6. Alternatively, the laser irradiation space 7 and/or the space between the first notch filter 31a and the second lens 32b of the fluorescence collecting optical system 3 may not be filled with the silicone resin.

As shown in FIG. 1, the space between the lenses 32a and 32b may not be filed with the silicone resin 6, and each of the two interfaces between this space and the silicon resin 6 may be shaped like a lens. Then, it is possible to use part of the resin 6 as the lenses, and therefore it is not necessary to provide separate lenses, which may be made from glass or other material. This reduces the number of parts.

That part of the resin which surrounds the optical path, through which the excitation light and the light including the fluorescence radiated from the sample pass, (i.e., resin that surrounds the space defining the optical path through which the excitation light and the fluorescence from the sample S proceed in the laser irradiation space 7 and the fluorescence collecting optical system 3) substantially uniformly contains a pigment that has wavelength characteristics to absorb the excitation light, the intrinsic fluorescence generated upon irradiation of the sample holding member with the excitation light, and the Raman light generated from the silicone resin upon passing of the excitation light through the silicone resin. An amount of the pigment is decided (set) to be able to entirely absorb the light which is generated in the space including the optical path, through which the excitation light and the light including the fluorescence radiated from the sample pass, and which proceeds out of the optical path. A black pigment is used in the laser-induced fluorescence measuring unit of this embodiment.

It should be noted that the pigment may not be substantially uniformly contained the above-mentioned part of the resin as long as it is possible to absorb all the light that is generated in the space including the optical path through which the excitation light and the light including the fluorescence radiated from the sample pass and that proceeds out of the optical path. For example, the pigment may be contained in the resin with a certain concentration distribution. Alternatively, the pigment may be contained in some areas of the above-mentioned part of the resin.

The laser-induced fluorescence measuring unit of this embodiment includes the resin 6 in which the fluorescence collecting optical system 3 that has the lenses, the optical filters and other components is embedded (buried). Therefore, the optical components such as the lenses and the optical filters are spatially (three-dimensionally) fixed by (in) the resin 6.

In other words, the optical components are entirely enclosed by the resin 6, and the positional displacements of the optical components hardly take place even if vibrations and impacts are applied to the laser-induced fluorescence measuring device. As a result, the misalignment of the fluorescence collecting optical system 3 is reduced or suppressed.

The above-described configuration does not need a rigid and large optical component holder, which is required in the conventional laser-induced fluorescence measuring device in order to cope with the vibrations and impacts applied to the laser-induced fluorescence measuring device. Thus, it is possible to make the fluorescence measuring device compact.

When the optical components are embedded in the silicone resin 6, it is possible to bring the resin 6 into contact with the optical components while purging the air from the interface between the resin 6 and the optical components. This results in good and tight contact between the resin 6 and the optical components. Accordingly, it is possible to substantially avoid undesired light reflection and scattering that would be caused if the air exists at the interface between the resin and the optical components.

As described above, the laser irradiation space 7 and the space including the fluorescence collecting optical system 3 are enclosed by the silicone resin 6 that contains the pigment having the capability of absorbing the laser beam L (i.e., the excitation light) and the intrinsic fluorescence generated upon irradiating the sample casing 2 with the laser beam L. The sample casing 2 carries the sample S.

The silicone resin 6 constituting the laser irradiation space 7 and the space for the fluorescence collecting optical system 3 is made from the same resin as silicone resin 61 that contains the pigment and encloses the resin 6. Thus, the refractive index of the resin 6 is the same as the refractive index of the resin 61. The resin 61 may be occasionally referred to as "pigment-containing silicone resin 61" in the following description. Therefore, there is not a boundary, in terms of refractive index, between the area occupied by the silicone resin 6 and the area occupied by the pigment-containing silicone resin 61. As such, when the light passing through the area occupied by the silicone resin 6 is incident to the area occupied by the pigment-containing silicone resin 61, the reflection and the scattering of the light hardly occur at the interface between the silicone resin 6 and the silicone resin 61.

It should be noted that slight light reflection may occur at the interface between the resin 6 and the pigment-containing resin 61 around the resin 6 or in the vicinity of the interface between the resin 6 and the pigment-containing resin 61 due to a complicated change in the refractive index dispersion in the vicinity of the interface between the resin 6 and the pigment-containing resin 61. In reality, however, it is assumed that the amount (content) of the contained pigment increases progressively relative to the resin at the interface between the resin 6 and the pigment-containing resin 61. Even if the light reflection occurs at the interface between the resin 6 and the pigment-containing resin 61, the intensity of the light reflection is very small and the reflected light hardly re-enters the resin 6 (will be described later).

In practice, it is also assumed that the amount of the contained pigment increases progressively at the interface between the pigment-containing resin 61 and other components and in the vicinity of end faces of the pigment-containing resin 61 (those faces which contact the air), like the interface between the resins 6 and 61. Thus, it is considered that the light reflection is relatively small at the surfaces of the pigment-containing resin 61.

The pigment contained in the pigment-containing silicone resin 61 has characteristics to absorb the laser beam L (i.e., excitation light), the intrinsic fluorescence generated upon irradiating the sample casing 2 of the sample S with the laser beam L, and the Raman light generated in the resin 6 upon passing of the excitation light in the silicone resin 6. Therefore, when the reflected light and/or the scattered light of the laser beam L, which is the excitation light, in the fluorescence collecting optical system 3 passes through the area occupied by the silicone resin 6 and is incident to the area occupied by the pigment-containing resin 61, for example, then the reflected light and the scattered light of the laser beam L is absorbed by the pigment contained in the pigment-containing silicone resin 61.

In other words, when the undesired reflected light and scattered light of the intrinsic fluorescence generated upon irradiating the sample casing 2, which has the sample S therein, with the laser beam L, and the undesired reflected light and scattered light of the laser beam L (excitation light) enter the interface between the resin 6, which defines the laser irradiation space 7 (space for holding the sample S that is irradiated with the laser beam L) and the space for the fluorescence collecting optical system 3, and the pigment-containing resin 61 around this space, then the light reflection takes place little at the interface. Most of the above-mentioned undesired reflected light and the scattered light are absorbed by the pigment contained in the pigment-containing resin 61. The above-mentioned undesired reflected light and the scattered light may collectively be referred to as "stray light" hereinafter. The stray light hardly returns to the laser irradiation space 7 and the space for the fluorescence collecting optical system 3.

In the laser irradiation space 7 and the space for the fluorescence collecting optical system 3, therefore, a complicated multiple reflection of the stray light of the laser beam L (excitation light) and the stray light of the intrinsic fluorescence generated upon irradiating the sample casing 2, which carries the sample S, with the laser beam L hardly takes place. Accordingly, the fluorescence collecting optical system 3 need not prepare for the above-mentioned complicated multiple reflection. Thus, the fluorescence collecting optical system 3 can have a simple structure, and in turn the laser-induced fluorescence measuring device of this embodiment can have a compact size. Most of the ambient light (outside light) is absorbed by the pigment contained in the pigment-containing resin 61. Accordingly, it is possible to prevent the ambient light from entering the fluorescence collecting optical system 3.

It should be noted that instead of using the pigment-containing resin 61 to absorb the stray light, resin that contains a dye (or dyes) capable of absorbing the laser beam L (i.e., excitation light) and the intrinsic fluorescence generated upon irradiating the sample casing 2, which carries the sample S, with the laser beam L may be included in the resin. However, the dye is different from the pigment in that the dye moves in the silicone resin. Thus, the boundary between the silicone resin and the dye-containing silicone resin becomes indistinct (vague). This may result in a problem. Specifically, in some cases, the dye may permeate the silicone resin 6 and penetrate the optical path of the fluorescence.

Consequently, it is preferred that the space (material) for absorbing the stray light is constituted by the pigment-containing silicone resin 61 in order to stably maintain the boundary between the space (laser irradiation space 7) in which the laser beam L (excitation light) proceeds and the space for absorbing the stray light, and the boundary between the space (space including the fluorescence collecting optical system 3) including the optical path in which the fluorescence radiated from the sample S proceeds up to the fluorescence measuring unit, and the space for absorbing the stray light.

Now, an exemplary configuration of the laser-induced fluorescence measuring device according to this embodiment will be described in detail.

(1) Silicone Resin

SIM-360 manufactured by Shin-Etsu Chemical Co., Ltd. was used as the silicone resin 6. This silicone resin is PDMS (polydimethylsiloxane), which is solidified at room temperature. The silicone resin was heaped up, like putty, on the components of the laser-induced fluorescence measuring device, such as the laser light source 1, the measurement sample S, the fluorescence collecting optical system 3, which includes the lenses, the optical filters, and other components, the photomultiplier tube 4 (fluorescence measuring unit), and the electric power supply 5 adapted to feed the electric power to the laser light source 1 and the fluorescence measuring unit. In this manner, the components of the laser-induced fluorescence measuring device were embedded in the silicone resin 6.

It should be noted that the silicone resin 6 is not limited to SIM-360 of Shin-Etsu Chemical Co., Ltd. For example, a separate mold may be prepared to mold other PDMS than the above-mentioned PDMS, and then the components of the laser-induced fluorescence measuring device may be embedded in the molded PDMS.

(2) Laser Light Source

The laser light source 1, which was used to emit the laser beam L or the excitation light, was a diode-pumped solid-state (DPSS) laser. The DPSS laser is driven by a battery, and used in, for example, a laser pointer. Specifically, a green laser device that emitted a laser beam at a wavelength of 532 nm, which was the second harmonic of the semiconductor-pumped (diode-pumped) Nd:YVO$_4$ laser (wavelength was 1064 nm), was used as the laser light source 1.

(3) Electric Power Source

A battery was used as the electric power source 5 to flexibly meet the outdoor-use demand for the POCT (point of care testing). The battery is placed in a battery box, which is embedded in the silicone resin 6. As described above, the laser light source 1 (DPSS laser) is driven by the battery placed in the battery box. Only the laser head of the DPSS laser is placed at a predetermined position to irradiate the sample S with the laser beam L. The laser head of the DPSS laser is connected with the electric power source 5 by a power feeding line. The power feeding line is also embedded in the silicone resin 6. The power feeding line is not shown in the drawings.

(4) Sample (Measurement Target)

In this embodiment, the measurement sample S was a kit that included an antibody light chain variable domain polypeptide and an antibody heavy chain variable domain polypeptide. One of the antibody light chain variable domain polypeptide and antibody heavy chain variable domain polypeptide is labelled by the fluorescent dye. This kit is referred to as, for convenience, "antibody labelled by the fluorescent material."

The "antibody labelled by the fluorescent material" is a piece of a recombinant antibody, with the distal end (terminus) and its vicinity of the antibody being fluorescently labelled by the dye. The simple substance of this antibody is in a quenched state, i.e., the fluorescence of the dye is quenched by an amino acid in the antibody. When an antigen, which becomes a sample S, is combined with the antibody labelled by the fluorescent material, the quenching is cancelled, and the fluorescence intensity of the dye significantly increases.

In other words, when the antibody labelled by the fluorescent material prior to the reaction with the antigen is irradiated with the laser beam, the fluorescence of the dye is not generated. However, when the "antibody labelled by the fluorescent material" that couples with the antigen is irradiated with the laser beam after the antibody labelled by the fluorescent material reacts with the antigen, an amount of the fluorescence from the dye increases.

When the above-described sample S is used, the antigen is poured in the "antibody labelled by the fluorescent material" in the container and mixed with the "antibody labelled by the fluorescent material." Then, the resulting liquid mixture is irradiated with the laser beam (i.e., excitation light), and the generated fluorescence is measured. Such easy measurement can show the coupling state (coupling condition) between the antigen and the antibody. In other words, a solidifying step for solidifying the antibody or the antigen in a microchip when the degree of the antibody-antigen reaction is measured with the microchip becomes unnecessary, and a cleaning step for removing nonspecific absorption of the labelling compound becomes unnecessary.

(5) Sample Casing

Figure 2:
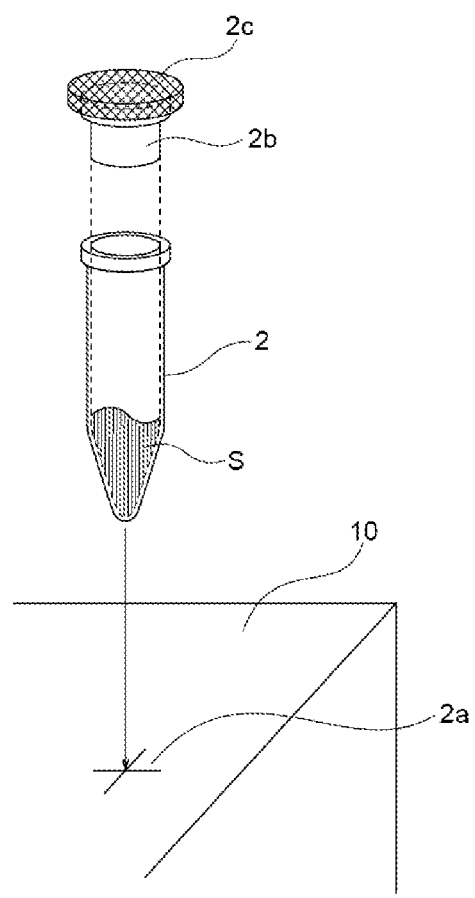
FIG. 2 is a view useful to describe placement of a sample casing that contains a sample therein.

FIG. 2 illustrates the installation of the sample casing that has the sample S therein. For example, a polystyrene-made PCR tube was used as the sample casing 2 to receive the "antibody labelled by the fluorescent material" and a solution containing the antigen. The PCR tube had a 5 mm diameter.

The sample casing 2 (PCR tube) shown in FIG. 2 has a tapered lower end, and therefore bubbles are difficult to be generated at the lower end of the PCR tube 2 even if the liquid "antibody labelled by the fluorescent material" and the solution containing the antigen are introduced (received). The PCR tube 2, into which the sample solution is introduced, is positioned in the main body 10 of the laser-induced fluorescence measuring device such that the lower end of the PCR tube is irradiated with the laser beam L emitted from the DPSS laser device shown in FIG. 1.

The sample casing 2 (PCR tube) that receives the sample S is sealed by a light-shielding cap 2b, which has a light-shielding part 2c to shield the light from the outside, provided at the top of the sample casing. Then, the sample casing 2 is inserted in the laser-induced fluorescence measuring device from a sample casing insert portion 2a formed in the main body 10 of the laser-induced fluorescence measuring device. The main body 10 is a housing made from silicone resin. It should be noted that water is present between the silicone resin 6 and the sample casing 2. The water is present to facilitate the insertion of the sample casing 2 into the silicone resin 6, and to purge the air that may exist between the silicone resin 6 and the sample casing 2.

If there is an air layer between the silicone resin 6 and the sample casing 2, then the light scattering takes place in the air layer. Specifically, when the air layer exists on the laser beam incident side of the sample casing 2 (between the sample casing 2 and the laser head), then part of the excitation light is scattered by the air layer, and a loss occurs in the laser beam that is directed to the sample S in the sample casing 2. Likewise, when the air layer exists on the fluorescence radiating side of the sample casing 2, then part of the fluorescence is scattered by the air layer, and a loss occurs in the fluorescence that is radiated from the sample casing 2.

Figure 3:
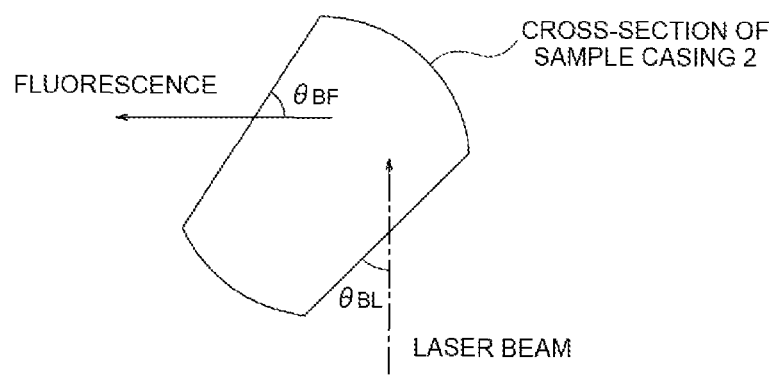
FIG. 3 is a view useful to describe a sample casing, with a laser beam incident plane of the sample casing being inclined at a Brewster's angle of the laser, and an emitting plane of the sample casing being inclined at a Brewster's angle of the fluorescence.

It should be noted that the sample casing 2 is not limited to the PCR tube. As shown in FIG. 3, for example, the sample casing 2 may be configured such that the laser beam incident plane of the sample casing 2 has an inclination of the Brewster's angle $\theta_{BL}$ of the laser, and the fluorescence emitting plane of the sample casing 2 has an inclination of the Brewster's angle $\theta_{BLF}$ of the fluorescence. With such configuration, the reflection of the p-polarized component of the laser at the laser incident plane is suppressed (reduced), and the reflection of the p-polarized component of the fluorescence at the fluorescence emitting plane is suppressed (reduced). Accordingly, it is possible to reduce a loss in the laser beam and a loss in the fluorescence.

The material of the sample casing 2 is not limited to polystyrene. For example, the sample casing 2 may be made from COC (Cyclic Olefin Copolymer). When the sample casing 2 is made from COC, the intensity of the intrinsic fluorescence generated upon light irradiation decreases, as compared to the sample casing made from polystyrene.

(6) Pigment-Containing Silicone Resin

As described above, the pigment-containing silicone resin 61 encloses the laser irradiation space 7 (i.e., space for holding the sample S irradiated with the laser beam L) and the space for the fluorescence collecting optical system 3, i.e., encloses optical path space for the laser beam L and the fluorescence. In the pigment-containing silicone resin 61, there are embedded the laser light source 1, the measurement sample S, the photomultiplier tube (fluorescence measuring unit) 4, and the electric power source (power supply) 5. The electric power source 5 feeds the electric power to the laser source 1 and the fluorescence measuring unit.

Thus, the pigment-containing silicone resin 61 constitutes the housing having a rectangular parallelepiped shape of the laser-induced fluorescence measuring device of this embodiment. This housing is made from resin.

It should be noted that although the black pigment is contained in the silicone resin region as mentioned above, the pigment is not limited to the black pigment. A pigment other than the black pigment may be used, as long as the pigment has wavelength characteristics to absorb the excitation light (i.e., laser beam L), the intrinsic fluorescence generated upon irradiating the sample casing 2 with the laser beam L, and the Raman light generated from the PDMS upon passing of the excitation light through the PDMS silicone resin 6 made from PDMS. The sample casing 2 holds the sample S.

Figure 4:
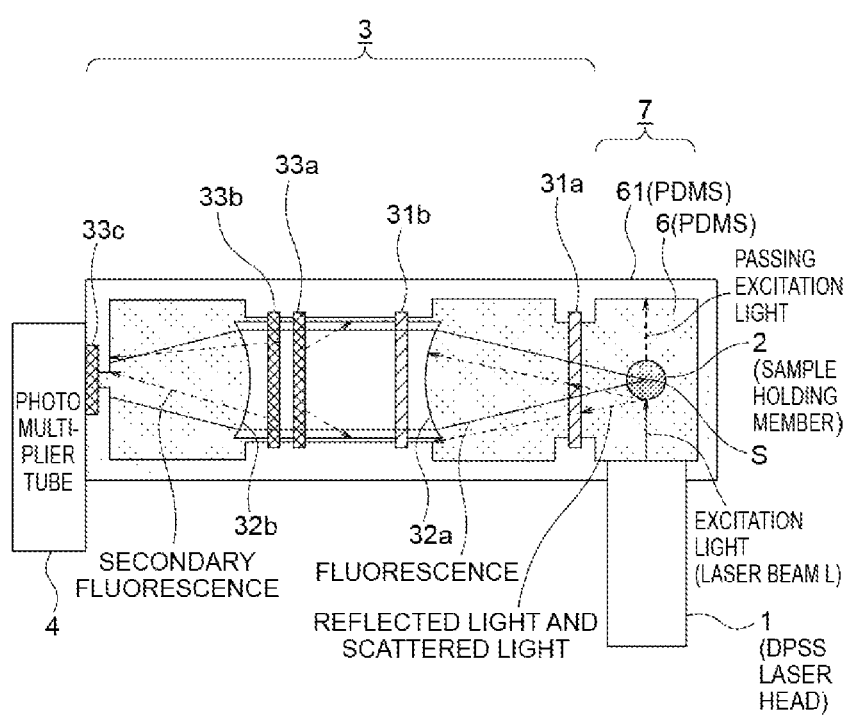
FIG. 4 illustrates an exemplary configuration of laser irradiation space and an optical system for collecting fluorescence.

Referring to FIG. 4, the amount of the pigment contained in the silicone resin region is decided such that the stray light derived from the excitation light and incident to the pigment-containing silicone resin 61, the stray light of the intrinsic fluorescence from the sample casing 2 and incident to the pigment-containing silicone resin 61, and the Raman light generated from the silicone resin (PDMS) 6 and incident to the pigment-containing silicone resin 61 are completely absorbed by the pigment in the realm of the laser irradiation space 7 and the fluorescence collecting optical system 3 shown in FIG. 4, i.e., such that the stray light derived from the excitation light and incident to the pigment-containing silicone resin 61, the stray light of the intrinsic fluorescence from the sample casing 2 and incident to the pigment-containing resin 61, and the Raman light generated from the silicone resin (PDMS) 6 and incident to the pigment-containing resin 61 are not emitted out of the laser-induced fluorescence measuring device. The pigment has a substantially uniform distribution in the pigment-containing silicone resin 61.

It should be noted that the pigment contained in the silicone resin region may not have a substantially uniform distribution as long as the silicon resin region can completely absorb the above-mentioned stray light and the Raman light. For example, the pigment contained in the silicone resin region may have a certain concentration distribution in the silicone resin region. Alternatively, the pigment may only be contained in some areas of the silicone resin region.

(7) Laser Irradiation Space

FIG. 4 shows the exemplary laser irradiation space 7 and the exemplary fluorescence collecting optical system 3. As described above, the laser irradiation space 7 receives the sample casing 2. The sample casing 2 has the sample S therein. The sample S is prepared by supplying the "antibody labelled by the fluorescent material" and the antigen from outside, mixing the antibody and the antigen with each other and bonding (combining) the antibody and the antigen with each other by the antibody-antigen reaction. The height position of the sample S in the sample casing 2 (position in a direction perpendicular to the drawing sheet of FIG. 4) is a position that is irradiated with the laser beam L having a 532 nm wavelength emitted from the laser light source 1 (DPSS laser head).

The laser irradiation space 7 is the space filled with the PDMS silicone resin 6 that is permeable to the wavelength of the laser beam L, the wavelength of the fluorescence radiated from the sample S and other wavelength. The laser irradiation space 7 is enclosed by the pigment-containing silicone resin 61 and the first notch filter 31a of the fluorescence collecting optical system 3.

As the sample S in the sample casing 2 is irradiated with the laser beam L, which is emitted from the laser light source 1 (DPSS laser head) at a wavelength of 532 nm, the fluorescence (at wavelength of 570-580 nm) is radiated from the dye of the "antibody labelled by the fluorescent material." The quenching (light extinction) condition of the "antibody labelled by the fluorescent material" is already canceled (removed) upon bonding between the antigen and the antibody.

The passing excitation light, which is directed to the sample S in the sample casing 2 but does not contribute to the excitation of the dye of the "antibody labelled by the fluorescent material" and passes through the sample casing 2, passes through the PDMS silicone resin 6, and is incident to the pigment-containing silicone resin 61. As described above, the excitation light (laser beam L) incident to the pigment-containing resin 61 is hardly reflected at the interface between the silicone resin 6 and the pigment-containing resin 61, and is absorbed by the pigment contained in the pigment-containing silicone resin 61. Thus, the above-mentioned passing excitation light is not incident to the fluorescence collecting optical system 3 as the stray light (reflected light or scattered light).

On the other hand, part of the laser beam L that is directed to the sample S from the laser light source 1 (DPSS laser head) is reflected and scatted at the surface of the sample casing 2, and that part of the laser beam L becomes the stray light that proceeds in various directions. Also, the intrinsic fluorescence, which depends on the material of the sample casing 2, is radiated from the laser beam radiated region of the sample casing 2. The intensity of the intrinsic fluorescence is smaller than the intensity of the stray light caused by the excitation light.

As the excitation light proceeds in the PDMS silicone resin 6, the Raman light is generated from the silicone resin 6 (PDMS). However, the intensity of the Raman light radiated from the silicone resin 6 (PDMS) is extremely small. Even if the Raman light is incident to the photomultiplier tube 4, which is the fluorescence measuring unit, it hardly affects the measurement results of the fluorescence measuring unit.

Out of the stray light caused by the excitation light and the stray light of the intrinsic fluorescence from the sample casing 2, that part of the stray light which is incident to the pigment-containing silicone resin 61 surrounding the laser irradiation space 7 is hardly reflected at the interface between the silicone resin 6 and the pigment-containing silicone resin 61, and is absorbed by the pigment contained in the pigment-containing silicone resin. Therefore, the passing excitation light does not enter the fluorescence collecting optical system 3 as the stray light (reflected light and/or scattered light).

Out of the stray light caused by the excitation light and the stray light of the intrinsic fluorescence from the sample casing 2, that part of the stray light which does not enter the pigment-containing silicone resin 61 surrounding the laser irradiation space 7 enters the first notch filter 31a of the fluorescence collecting optical system 3. The Raman light from the silicone resin 6 (PDMS) also enters the first notch filter 31a.

(8) Fluorescence Collecting Optical System

As shown in FIG. 4, the fluorescence collecting optical system 3 has the first notch filter 31a, the first lens 32a, the second notch filter 31b, the first color glass filter 33a, the second color glass filter 33b, the second lens 32b, the aperture 34, and the third color glass filter 33c from the sample side.

Each of the first notch filter 31a and the second notch filter 31b reflects the excitation light and the light in the wavelength region next to the excitation light, and transmits the light in the other wavelength regions. Specifically, when the excitation light has a 532 nm wavelength, then the light having a neighboring wavelength (wavelength near 532 nm) is reflected by the first notch filter 31a and the second notch filter 31b.

(a) First Notch Filter

As the stray light caused by the excitation light and derived from the laser irradiation space 7, the stray light of the intrinsic fluorescence from the sample casing 2 and derived from the laser irradiation space 7, and part of the Raman light from the PDMS and derived from the laser irradiation space 7 are incident to the first notch filter 31a, the stray light caused by the excitation light having a 532 nm wavelength is reflected by the first notch filter 31a, and the stray light of the intrinsic fluorescence from the sample casing 2 simply passes through the first notch filter 31a.

The fluorescence (at wavelength 570-580 nm), which is the measurement target, from the dye of the "antibody labelled by the fluorescent material" of which the quenching condition is cancelled by the bonding of the antibody with the antigen also simply passes through the first notch filter 31a. In the following description, the fluorescence having the 570-580 nm wavelength is referred to as the measurement target fluorescence.

The first notch filter 31a has the indent angle dependency. When the light having the 532 nm wavelength is incident at the incident angle of 0 degree, the light is reflected nearly 100% by the first notch filter 31a. On the other hand, when the light having the 532 nm wavelength is incident at the incident angle greater than 0 degree, then part of the light is not reflected; instead, part of the light passes through the first notch filter 31a.

As described above, the stray light caused by the excitation light proceeds in various directions. Thus, the incident angle of part of the stray light that is incident to the first notch filter 31a is not always 0 degree. Accordingly, the stray light that is incident to the first notch filter 31a is attenuated, but it passes through the first notch filter 31a.

The stray light caused by the excitation light, which is partly reflected by the first notch filter 31a, returns to the laser irradiation space 7, and is incident to the pigment-containing silicone resin 61 surrounding the laser irradiation space 7. Thus, the stray light is absorbed by the pigment contained in the pigment-containing silicone resin 61.

(b) First Lens

In this embodiment, as described above, the transparent (permeable) silicone resin 6 is not provided between the first lens 32a and the second lens 32b. In other words, the space between the first lens 32a and the second lens 32b is the hollow space. The transparent silicone resin 6 fills between the hollow space and the first notch filter 31a, and an end face of the transparent silicone resin 6 on the hollow space side has a lens shape. In other words, the end face of the transparent silicone resin 6 defines (forms) the first lens 32a.

The stray light caused by the excitation light that passes the first notch filter 31a, the stray light of the intrinsic fluorescence from the sample casing 2 that passes the first notch filter 31a, the Raman light from the silicone resin 6 (PDMS) that passes the first notch filter 31a, and the measurement target fluorescence at the wavelength of 570-580 nm that passes the first notch filter 31a are incident to the first lens 32a. There is a possibility that the Raman light is generated when the stray light caused by the excitation light passes through the PDMS silicone resin 6 that fills the space between the first notch filter 31a and the first lens 32a.

However, even if the Raman light is generated, the intensity of the Raman light is extremely small because the Raman light is generated by the stray light caused by the excitation light. If the Raman light is generated, the Raman light is incident to the first lens 32a.

The first lens 32a is a condenser lens (condensing lens), and serves as a collimator lens (collimating lens) to convert (transform) the incident light to parallel light in this embodiment. Accordingly, the stray light caused by the excitation light that is incident to the first lens 32a, the stray light of the intrinsic fluorescence from the sample casing 2 that is incident to the first lens 32a, the Raman light from the silicone resin 6 (PDMS) that is incident to the first lens 32a, and the measurement target fluorescence at the wavelength of 570-580 nm that is incident to the first lens 32a pass through the first lens 32a as the parallel light.

The stray light caused by the excitation light that is partly reflected at the surface of the first lens 32a, the stray light of the intrinsic fluorescence from the sample casing 2 that is partly reflected at the surface of the first lens 32a, the Raman light from the silicone resin 6 (PDMS) that is partly reflected at the surface of the first lens 32a, and the measurement target fluorescence at the wavelength of 570-580 nm that is partly reflected at the surface of the first lens 32a enter the pigment-containing silicone resin 61 that surrounds the space between the first notch filter 31a and the first lens 32a, and are absorbed by the pigment contained in the pigment-containing silicone resin 61. Part of the stray light caused by the excitation light, which does not enter the pigment-containing silicone resin 61 and is incident again to the first notch filter 31a, part of the stray light of the intrinsic fluorescence from the sample casing 2, which does not enter the pigment-containing silicone resin 61 and is incident again to the first notch filter 31a, and part of the measurement target fluorescence, which does not enter the pigment-containing silicone resin 61 and is incident again to the first notch filter 31a, are reflected by the first notch filter 31a again and directed toward the first lens 32a. However, the intensity of the above-mentioned parts of the stray light and the measurement target fluorescence is extremely small. Even if the above-mentioned parts of the stray light and the measurement target fluorescence are incident to the photomultiplier tube (fluorescence measuring unit) 4, they hardly affect measurement results of the fluorescent measuring unit, and therefore they are not taken into account in this embodiment. Out of the light that is incident again to the first notch filter 31a, that part of the light which passes through the first notch filter 31a is incident to the pigment-containing silicone resin 61 around the laser irradiation space 7 and absorbed by the pigment contained in the pigment-containing silicone resin 61.

It should be noted that if the pigment-containing silicone resin 61 around the space between the first notch filter 31a and the first lens 32a is not provided, but a simple wall is provided as in the conventional configuration, then it is necessary for the wall to have a concave-convex labyrinth structure in order to block (shield) the stray light. Thus, the structure of the fluorescence collecting optical system 3 of the conventional laser-induced fluorescence measuring device becomes complicated and large. In the embodiment of the present invention, on the contrary, the fluorescence measuring device has the pigment-containing silicone resin 61 around the space between the first notch filter 31a and the first lens 32a, and therefore the fluorescence measuring device of this embodiment does not need a concave-convex labyrinth structure, unlike the conventional configuration. Accordingly, the fluorescence collecting optical system 3 of the laser-induced fluorescence measuring device of this embodiment can have a compact structure, as compared to the conventional configuration.

(c) Second Notch Filter

The stray light caused by the excitation light which passes through the first lens 32a, the stray light of the intrinsic fluorescence from the sample casing 2 which passes through the first lens 32a, the Raman light from the PDMS which passes through the first lens 32a, and the measurement target fluorescence at a wavelength of 570-580 nm which passes through the first lens 32a are all incident to the second notch filter 31b. The second notch filter 31b is located in the vicinity of the first lens 32a.

Because the light incident to the second notch filter 31b is all the parallel light, the incident angle of the stray light caused by the excitation light, which is incident to the second notch filter 31b, is zero (0) degree. Thus, most of the stray light caused by the excitation light, which is incident to the second notch filter 31b, is reflected toward the first lens 32a by the second notch filter 31b. It should be noted that an additional notch filter may be attached to the first notch filter 31a to eliminate (remove) the Raman scattering generated by the silicone resin (PDMS) if necessary under given conditions. Specifically, the first notch filter may preferably be designed such that the first notch filter can selectively reflect the light at wavelengths of 545, 550, 627 and 630 nm when the incident light has a wavelength of 532 nm.

The stray light caused by the excitation light, which is reflected in the above-described manner, is incident to the pigment-containing silicone resin 61, which surrounds (encloses) the space between the first notch filter 31a and the first lens 32a, and absorbed by the pigment contained in the pigment-containing silicone resin 61. It should be noted that part of the stray light caused by the excitation light, which is not incident to the pigment-containing silicon resin 61 but is re-incident to the first notch filter 31*a*, part of the stray light of the intrinsic fluorescence from the sample casing 2, which is not incident to the pigment-containing silicon resin 61 but is re-incident to the first notch filter 31*a*, and part of the measurement target fluorescence, which is not incident to the pigment-containing silicon resin 61 but is re-incident to the first notch filter 31*a*, are reflected by the first notch filter 31*a* and/or pass through the first notch filter 31*a*. However, these parts of the stray light and fluorescence have very small intensity. Therefore, even if these parts of the stray light and fluorescence are incident to the photomultiplier tube 4 (fluorescence measuring unit), they hardly affect the measuring results of the fluorescence measuring unit. Thus, these parts of the stray light and fluorescence are not taken into account in this embodiment.

The stray light of the intrinsic fluorescence from the sample casing 2, the Raman light from the PDMS, and the measurement target fluorescence having the 570-580 nm wavelength, which have wavelength different from the stray light caused by the excitation light at the wavelength of 532 nm, pass through the second notch filter 31*b*.

(d) First and Second Color Glass Filters

The stray light caused by the excitation light, which is significantly attenuated by the second notch filter 31*b*, the stray light of the intrinsic fluorescence from the sample casing 2, which passes through the second notch filter 31*b*, the Raman light from the PDMS, which passes through the second notch filter 31*b*, and the measurement target fluorescence at the wavelength of 570-580 nm, which passes through the second notch filter 31*b*, are incident to the first and second color glass filters 33*a* and 33*b*.

Part of the above-mentioned light incident to the first color glass filter 33*a* is reflected at the surface of the first color glass filter 33*a*. Part of the reflected light is incident to the pigment-containing resin 61 around the space between the first color glass filter 33*a* and the second notch filter 31*b*, and absorbed by the pigment contained in the pigment-containing silicone resin 61.

As mentioned above, the transparent silicone resin 6 does not fill between the first lens 32*a* and the second lens 32*b*, i.e., the hollow space is present between the first lens 32*a* and the second lens 32*b*. Part of the light, which is incident from this hollow space to the silicone resin 6 and the pigment-containing silicone resin 61 around this hollow space, is reflected at the resin surface.

Part of such light is absorbed by the first color glass filter 33*a* and the second color glass filter 33*b*. The remainder of the light is incident to the space, which is filled with the transparent silicone resin 6 between the second lens 32*b* and the third color glass filter 33*c* via the second lens 32*b*, and is incident to the pigment-containing silicone 61 around this space. Thus, the remainder of the light is absorbed by the pigment contained in the pigment-containing silicone resin 61.

It should be noted that the light, which is not incident to the pigment-containing silicone resin 61 but is re-incident to the second notch filter 31*b*, is reflected at the surface of the second notch filter 31*b* or passes through the second notch filter 31*b*. However, the intensity of such light is extremely small. Even if such light is incident to the photomultiplier tube 4 (fluorescence receiving unit or detector), it hardly influences measuring results.

Each of the first and second color glass filters 33*a* and 33*b* is designed to transmit the measurement target fluorescence at the wavelength of 570-580 nm and absorb the light at other wavelengths. Thus, when the stray light caused by the excitation light and significantly attenuated by the second notch filter 31*b* is incident to the first and second color glass filters 33*a* and 33*b*, the stray light of the intrinsic fluorescence from the sample casing 2 which passes through the second notch filter 31*b* is incident to the first and second color glass filters 33*a* and 33*b*, and the Raman light from the PDMS which passes through the second notch filter 31*b* is incident to the first and second color glass filters 33*a* and 33*b*, then these stray light and the Raman light are absorbed by the first and second color glass filters 33*a* and 33*b* and converted to a thermal energy. Two color glass filters (i.e., first and second color glass filters 33*a* and 33*b*) are used in this embodiment because the light other than the measurement target fluorescence having the 570-580 nm wavelength is almost completely absorbed by the two color glass filters. It should be noted that if the first color glass filter 33*a* is able to absorb the light other than the measurement target fluorescence having the 570-580 nm wavelength to the extent that the influence on measuring results of the photomultiplier tube 4 (fluorescence measuring unit) becomes negligible, the second color glass filter 33*b* may be dispensed with.

However, when the stray light caused by the excitation light and significantly attenuated by the second notch filter 31*b* is incident to and absorbed by the first and second color glass filters 33*a* and 33*b* and converted to the thermal energy, the stray light of the intrinsic fluorescence from the sample casing 2 which passes through the second notch filter 31*b* is incident to and absorbed by the first and second color glass filters 33*a* and 33*b* and converted to the thermal energy, and the Raman light from the PDMS which passes through the second notch filter 31*b* is incident to and absorbed by the first and second color glass filters 33*a* and 33*b* and converted to the thermal energy, then secondary fluorescence is emitted from the first and second color glass filters 33*a* and 33*b*. In experiments conducted by the inventors, the secondary fluorescence emitted from the color glass filters was red light that belonged to a wavelength region near about 660 nm.

The secondary fluorescence is emitted in any direction on the light incident side of the first color glass filter 33*a* and on the light emitting side of the second color glass filter 33*b*.

Part of the second fluorescence emitted on the light incident side of the first color glass filter 33*a* is incident to the pigment-containing silicone resin 61 around the space between the first color glass filter 33*a* and the second notch filter 31*b* and absorbed by the pigment contained in the pigment-containing silicone resin 61.

Part of the light directed toward the pigment-containing silicone resin 61 is reflected at the resin surface, and part of the reflected light is incident to the space that is filled with the transparent silicone resin 6 between the second lens 32*b* and the third color glass filter 33*c* via the first and second color glass filters 33*a* and 33*b* and the second lens 32*b* such that it is incident to the pigment-containing silicone resin 61 around the space (transparent silicone resin 6) and absorbed by the pigment contained in the pigment-containing silicone resin 61.

The light, which is not incident to the pigment-containing silicone resin 61 but re-incident to the second notch filter 31*b*, is reflected at the surface of the second notch filter 31*b* or passes through the second notch filter 31*b*. However, the intensity of such light is extremely small. Even if such light is incident to the photomultiplier tube 4 (fluorescence measuring unit), it hardly influences the measuring results of the photomultiplier. Thus, such light is not taken into account in this embodiment.

(e) Spatial Filter (Second Lens 32b and Aperture 34)

The measurement target fluorescence having the 570-580 nm wavelength and passing through the second color glass filter 33b, and the secondary fluorescence radiated from the first and second color glass filters 33a and 33b are incident to the second lens 32b.

In this embodiment, as described above, the space between the first lens 32a and the second lens 32b is the hollow space. That end face of the transparent silicone resin 6 between the hollow space and the aperture 34, which is on the hollow space side, has the lens shape. Thus, one end face of the transparent silicone resin 6 defines the second lens 32b. The second lens 32b is located in the vicinity of the second color glass filter 33b.

The second lens 32b is a condenser lens. The aperture 34 is formed in the vicinity of the light condensing (concentrating) position of the measurement target fluorescence (parallel light) having the 570-580 nm wavelength. The aperture 34 has a pinhole shape, and is present on the optical axis of the measurement target fluorescence having the 570-580 nm wavelength.

As shown in FIG. 4, the opening side of the aperture 34 of the fluorescence collecting optical system 3 in this embodiment is occupied by the PDMS silicone resin 6, and the shielding side of the aperture 34 is occupied by the pigment-containing silicone resin 61.

As described above, the wavelength of the secondary fluorescence radiated from the first and second color glass filters 33a and 33b belongs to the wavelength region near about 660 nm, and therefore is different from the 570-580 nm wavelength of the measurement target fluorescence. Therefore, out of the secondary fluorescence radiated in any direction on the light emitting side of the second color glass filter 33b, the light that is incident to the second lens 32b at the 0-degree incident angle is condensed to a position different from the light condensing position of the measurement target fluorescence having the 570-580 nm wavelength because of the chromatic aberration of the second lens 32b. That part of the secondary fluorescence which is incident at an angle other than the 0-degree incident angle proceeds along a different optical path from the secondary fluorescence that is incident at the 0-degree incident angle. Accordingly, most of the secondary fluorescence does not pass through the aperture 34, and is directed to the shielding part of the aperture 34. In other words, the second lens 32b and the aperture 34 serve in combination as a spatial filter that selectively transmits the 570-580 nm wavelength of the measurement target fluorescence.

A very small amount of the secondary fluorescence passes through the aperture, but such amount of the secondary fluorescence hardly influences the measuring results of the photomultiplier tube 4 (fluorescence measuring unit) even if the secondary fluorescence is incident to the photomultiplier tube 4.

(e) Third Color Glass Filter

The measurement target fluorescence having the 570-580 nm wavelength that passes through the aperture 34 and the secondary fluorescence that passes through the aperture 34 are incident to the third color glass filter 33c disposed on the light emitting side of the aperture 34. The light emitting side (face) of the third color glass filter 33c is adjacent to the light receiving part of the photomultiplier tube 4 (fluorescence measuring unit).

The third color glass filter 33c is designed to transmit the measurement target fluorescence having the 570-580 nm wavelength and absorb the light having other wavelength regions. The third color glass filter 33c serves as a protection filter for the photomultiplier tube 4, and hardly transmits the light other than the measurement target fluorescence having the 570-580 nm wavelength.

Now, the light absorption at the boundary (interface) between the silicone resin 6 and the pigment-containing silicone resin 61 will be described.

When the stray light caused by the excitation light, the stray light of the intrinsic fluorescence from the sample casing, the Raman light generated from the PDMS and other light are incident to the pigment-containing silicone resin 61 from the silicone resin 6, the stray light, the Raman light and other light are quickly absorbed by the pigment contained in the pigment-containing silicone resin 61, as described above. Although the refractive index of the silicone resin 6 is equal to the refractive index of the pigment-containing silicone resin 61, the refractive index dispersion may change in a complicated manner in the vicinity of an area where the light is quickly absorbed. Then, light reflection may slightly occur at or in the vicinity of the interface between the silicone resin 6 and the pigment-containing silicone resin 61 because of the complicated change of the refractive index dispersion at or in the vicinity of the interface between the silicone resins 6 and 61.

In reality, however, the above-mentioned light reflection is extremely small because it is considered that the content of the pigment relative to the resin progressively increases at the interface between the silicone resin 6 and the pigment-containing silicone resin 61, as described above.

Figure 5:
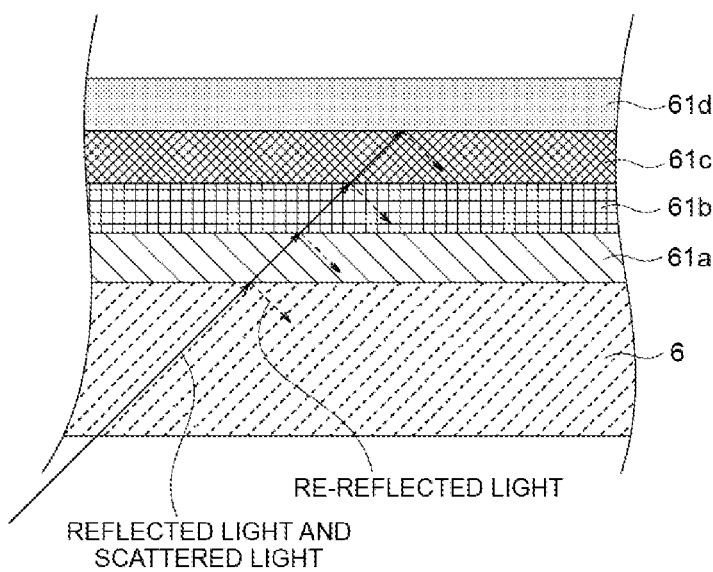
FIG. 5 schematically depicts the stepwise increase of an amount of a contained pigment relative to resin.
Figure 6:
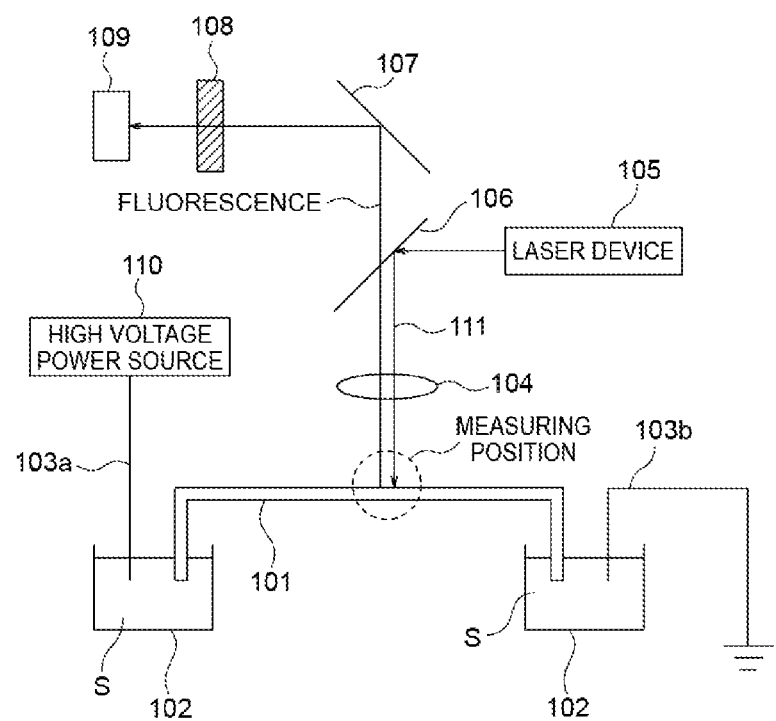
FIG. 6 illustrates an exemplary configuration of an antigen measuring device that uses the LIF method.

FIG. 5 schematically illustrates the progressive increase of the content (amount) of the pigment relative to the resin at the interface between the silicone resin 6 and the pigment-containing silicone resin 61. For the sake of easier understanding, the pigment-containing silicone resin 61a, the pigment-containing silicone resin 61b, the pigment-containing silicone resin 61c, and the pigment-containing silicone resin 61d are laminated in this order such that the content of the pigment relative to the silicone resin 6 increases stepwise, not progressively.

In this configuration, the difference between the pigment content of the pigment-containing silicone resin 61a and the silicone resin 6 is smaller than the difference between the pigment content of the pigment-containing silicone resin 61d and the silicone resin 6, the difference between the pigment content of the pigment-containing silicone resin 61a and the pigment content of the pigment-containing silicone resin 61b is smaller than the difference between the pigment content of the pigment-containing silicone resin 61d and the silicone resin 6, the difference between the pigment content of the pigment-containing silicone resin 61b and the pigment content of the pigment-containing silicone resin 61c is smaller than the difference between the pigment content of the pigment-containing silicone resin 61d and the silicone resin 6, and the difference between the pigment content of the pigment-containing silicone resin 61c and the pigment content of the pigment-containing silicone resin 61d is smaller than the difference between the pigment content of the pigment-containing silicone resin 61d and the silicone resin 6.

Thus, when the stray light caused by the excitation light, the stray light of the intrinsic fluorescence from the sample casing 2, and the Raman light generated from the PDMS are incident to the pigment-containing silicone resin 61a from the silicone resin 6, the amount of such light to be absorbed by the pigment-containing silicone resin 61a is smaller than the amount to be absorbed by the silicone resin 61d when the light is directly incident to the pigment-containing silicone resin 61d from the silicone resin 6.

Therefore, the change in the light absorption in the vicinity of the interface between the silicone resin 6 and the pigment-containing silicone resin 61a is smaller than when the light is directly incident to the pigment-containing silicone resin 61d from the silicone resin 6. Accordingly, the change in the refractive index dispersion is also small in the vicinity of an area where the light absorption takes place.

As such, when the light reflection takes place at or in the vicinity of the interface between the silicone resin 6 and the pigment-containing silicone resin 61a, the intensity of the light reflection is relatively small.

On the other hand, the amount of the light to be absorbed by the pigment-containing silicone resin 61a is small, as described above. Thus, when the stray light caused by the excitation light, the stray light of the intrinsic fluorescence from the sample casing 2, and the Raman light generated from the PDMS are incident to the pigment-containing silicone resin 61a, the stray light and the Raman light are not completely absorbed by the pigment-containing silicone resin 61a, and are incident to the pigment-containing silicone resin 61b.

The amount of the light to be absorbed by the pigment-containing silicone resin 61b is also relatively small, as in the case of absorption by the pigment-containing silicone resin 61a. Therefore, the change in the light absorption in the vicinity of the interface between the pigment-containing silicone resin 61a and the pigment-containing silicone resin 61b is relatively smaller, and the change in the refractive index dispersion is also small in the vicinity of an area where the light absorption takes place.

As such, when the light reflection takes place at or in the vicinity of the interface between the pigment-containing silicone resin 61a and the pigment-containing silicone resin 61b, the intensity of the light reflection is smaller than when the light is directly incident to the pigment-containing silicone resin 61d from the silicone resin 6. The reflected light passes through the pigment-containing silicone resin 61a again, and is absorbed by the pigment-containing silicone resin 61a. Therefore, the reflected light hardly enters the silicone resin 6.

On other hand, the amount of the light absorbed by the pigment-containing resin 61b is small, as described above. Thus, the stray light caused by the excitation light which is incident to the pigment-containing silicone resin 61b, the stray light of the intrinsic fluorescence from the sample casing 2 which is incident to the pigment-containing silicone resin 61b, and the Raman light generated from the PDMS which is incident to the pigment-containing silicone resin 61b are not completely absorbed by the pigment-contained resin 61b but incident to the pigment-containing silicone resin 61c. The intensity of the light incident to the pigment-containing silicone resin 61c is smaller than the intensity of the light incident to the pigment-containing silicone resin 61b from the pigment-containing silicone resin 61a.

The stray light caused by the excitation light which is incident to the pigment-containing silicone resin 61c, the stray light of the intrinsic fluorescence from the sample casing 2 which is incident to the pigment-containing silicone resin 61c, and the Raman light generated from the PDMS which is incident to the pigment-containing silicone resin 61c are absorbed by the pigment-containing silicone resin 61c in a relatively small amount.

Thus, the change in the light absorption in the vicinity of the interface (boundary) between the pigment-containing silicone resin 61b and the pigment-containing silicone resin 61c is smaller than when the light is directly incident to the pigment-containing silicone resin 61d from the silicone resin 6. Accordingly, the change in the refractive index dispersion is small in the vicinity of an area where the light absorption occurs.

As such, when the light reflection occurs at or in the vicinity of the interface between the pigment-containing silicone resin 61b and the pigment-containing silicone resin 61c, the intensity of the light reflection is smaller than when the light is directly incident to the pigment-containing silicone resin 61d from the silicone resin 6. When the light reflection occurs at or in the vicinity of the interface between the pigment-containing silicone resin 61b and the pigment-containing silicone resin 61c, the reflected light passes through the pigment-containing silicone resin 61b again. Thus, the reflected light is absorbed by the pigment-containing silicone resin 61b, and hardly enters the pigment-containing silicone resin 61a. Even if a very small amount of the light enters the pigment-containing silicone resin 61a, this light passes through the pigment-containing silicone resin 61a, and is absorbed by the pigment-containing silicone resin 61a. Thus, the light hardly enters the area occupied by the silicone resin 6.

The amount of the light absorbed by the pigment-containing resin 61c is small. Thus, the stray light caused by the excitation light which is incident to the pigment-containing silicone resin 61c, the stray light of the intrinsic fluorescence from the sample casing 2 which is incident to the pigment-containing silicone resin 61c, and the Raman light generated from the PDMS which is incident to the pigment-containing silicone resin 61c are not completely absorbed by the pigment-contained resin 61c but incident to the pigment-containing silicone resin 61d. The intensity of the light incident to the pigment-containing silicone resin 61d is smaller than the intensity of the light incident to the pigment-containing silicone resin 61c from the pigment-containing silicone resin 61a.

The stray light caused by the excitation light which is incident to the pigment-containing silicone resin 61d, the stray light of the intrinsic fluorescence from the sample casing 2 which is incident to the pigment-containing silicone resin 61d, and the Raman light generated from the PDMS which is incident to the pigment-containing silicone resin 61d are absorbed by the pigment-containing silicone resin 61d in a small amount. Thus, the change in the light absorption in the vicinity of the interface (boundary) between the pigment-containing silicone resin 61c and the pigment-containing silicone resin 61d is smaller than when the light is directly incident to the pigment-containing silicone resin 61d from the silicone resin 6. Accordingly, the change in the refractive index dispersion is also small in the vicinity of an area where the light absorption occurs.

As such, when the light reflection occurs at or in the vicinity of the interface between the pigment-containing silicone resin 61c and the pigment-containing silicone resin 61d, the intensity of the light reflection is smaller than when the light is directly incident to the pigment-containing silicone resin 61d from the silicone resin 6. When the light reflection occurs at or in the vicinity of the interface between the pigment-containing silicone resin 61c and the pigment-containing silicone resin 61d, the reflected light passes through the pigment-containing silicone resin 61c again.

Thus, the reflected light is absorbed by the pigment-containing silicone resin 61*c*, and hardly enters the pigment-containing silicone resin 61*b*.

The intensity of the light incident to the pigment-containing silicone resin 61*d* is extremely small. Therefore, even if the above-mentioned light reflection takes place, it is assumed that the reflected light is almost absorbed by (in) the pigment-containing silicone resin 61*c*. Thus, the reflected light hardly re-enters the area occupied by the silicone resin 6.

On the other hand, the intensity of the light incident to the pigment-containing silicone resin 61*d* is extremely small, as described above. Thus, the light is entirely absorbed by the pigment-containing silicone resin 61*d*, and is not released out of the laser-induced fluorescence measuring device.

In the foregoing, the amount of the contained pigment increases stepwise relative to the silicone resin 6. However, the same explanation applies when the amount of the contained pigment increases progressively (linearly, continuously) relative to the silicone resin 6. When a plurality of pigment-containing silicone resin layers are formed such that the amount of the pigment increases progressively relative to the silicone resin, the light reflection at the interface between the silicone layers has a small intensity even if such light reflection occurs. Thus, the reflected light hardly re-enters the silicone resin.

REFERENCE NUMERALS AND SIGNS

1: Laser light source
2: Sample casing
2*a*: Insert part of the sample casing
2*b*: Light shielding cap
2*c*: Light shielding part
3: Fluorescence collecting optical system
4: Photomultiplier tube
5: Electric power source
6: Silicone resin
7: Laser irradiation space
10: Main body of the laser-induced fluorescence measuring device
31*a*: First notch filter
31*b*: Second notch filter
32*a*: First lens
32*b*: Second lens
33*a*: First color glass filter
33*b*: Second color glass filter
33*c*: Third color glass filter
34: Aperture
61: Pigment-containing silicone resin
L: Laser beam
S: Measurement sample

The invention claimed is:

1. A light-induced fluorescence measuring device comprising:
   a solid light source;
   a sample holding member configured to hold a sample;
   a fluorescence measuring unit configured to detect fluorescence emitted from the sample held by the sample holding member;
   a fluorescence collecting optical system configured to collect the fluorescence emitted from the sample and optically guide the fluorescence to the fluorescence measuring unit;
   a first resin material in which the sample holding member and the fluorescence collecting optical system are embedded; and
   a second resin material configured to enclose the first resin material,
   the sample holding member being permeable to light emitted from the solid light source and the fluorescence radiated from the sample, the light emitted from the solid light source being excitation light,
   the first resin material being permeable to the excitation light emitted from the solid light source and light including the fluorescence radiated from the sample, at least part of an optical path of the fluorescence collecting optical system for optically guiding the fluorescence being filled with the first resin material, and the first resin material forming a housing for holding the sample holding member and the fluorescence collecting optical system,
   said second resin material containing a pigment that has a wavelength characteristic to absorb the excitation light, intrinsic fluorescence generated upon irradiating the sample holding member with the excitation light, and Raman light generated from the first resin material when the excitation light proceeds in the first resin material, and
   an amount of the pigment to be contained being set to a value that completely absorbs light, which is generated in a space including the optical path for the excitation light and the light including the fluorescence radiated from the sample and which proceeds out of the optical path.

2. The light-induced fluorescence measuring device according to claim 1, wherein the fluorescence collecting optical system has at least one lens, a notch filter, and a color glass filter.

3. The light-induced fluorescence measuring device according to claim 2, wherein said at least one lens includes two lenses, the fluorescence collecting optical system has a hollow space, which is not filled with the first resin material, and two interfaces between the hollow space and the first resin material forms the two lens, respectively.

4. The light-induced fluorescence measuring device according to claim 2, wherein the fluorescence collecting optical system has, from an incident side of the excitation light and the light including the fluorescence radiated from the sample, a first notch filter configured to reflect light having a wavelength of the excitation light emitted from the solid light source, a first lens configured to convert the excitation light and the light including the fluorescence radiated from the sample into parallel light, a second notch filter configured to reflect the light having the wavelength of the excitation light, a first color glass filter configured to absorb light other than the fluorescence radiated from the sample, a second lens configured to condense the light including the fluorescence, and an aperture formed on an optical axis of the second lens and situated in the vicinity of a fluorescence condensing position.

5. The light-induced fluorescence measuring device according to claim 1, wherein the sample held by the sample holding member includes a kit that has an antibody light chain variable domain polypeptide and an antibody heavy chain variable domain polypeptide, with one of the antibody light chain variable domain polypeptide and the antibody heavy chain variable domain polypeptide being labelled by a fluorescent dye.

6. The light-induced fluorescence measuring device according to claim 3, wherein the fluorescence collecting optical system has, from an incident side of the excitation light and the light including the fluorescence radiated from the sample, a first notch filter configured to reflect light having a wavelength of the excitation light emitted from the solid light source, a first lens configured to convert the excitation light and the light including the fluorescence radiated from the sample into parallel light, a second notch filter configured to reflect the light having the wavelength of the excitation light, a first color glass filter configured to absorb light other than the fluorescence radiated from the sample, a second lens configured to condense the light including the fluorescence, and an aperture formed on an optical axis of the second lens and situated in the vicinity of a fluorescence condensing position.

7. The light-induced fluorescence measuring device according to claim 2, wherein the sample held by the sample holding member includes a kit that has an antibody light chain variable domain polypeptide and an antibody heavy chain variable domain polypeptide, with one of the antibody light chain variable domain polypeptide and the antibody heavy chain variable domain polypeptide being labelled by a fluorescent dye.

8. The light-induced fluorescence measuring device according to claim 3, wherein the sample held by the sample holding member includes a kit that has an antibody light chain variable domain polypeptide and an antibody heavy chain variable domain polypeptide, with one of the antibody light chain variable domain polypeptide and the antibody heavy chain variable domain polypeptide being labelled by a fluorescent dye.

9. The light-induced fluorescence measuring device according to claim 4, wherein the sample held by the sample holding member includes a kit that has an antibody light chain variable domain polypeptide and an antibody heavy chain variable domain polypeptide, with one of the antibody light chain variable domain polypeptide and the antibody heavy chain variable domain polypeptide being labelled by a fluorescent dye.

10. The light-induced fluorescence measuring device according to claim 6, wherein the sample held by the sample holding member includes a kit that has an antibody light chain variable domain polypeptide and an antibody heavy chain variable domain polypeptide, with one of the antibody light chain variable domain polypeptide and the antibody heavy chain variable domain polypeptide being labelled by a fluorescent dye.

11. The light-induced fluorescence measuring device according to claim 1, wherein the solid light source includes a laser light source, and the light-induced fluorescence measuring device is a laser-induced fluorescence measuring device.

12. The light-induced fluorescence measuring device according to claim 1, wherein the fluorescence measuring unit includes a photomultiplier tube.

13. The light-induced fluorescence measuring device according to claim 1, wherein the first resin material includes silicone, acryl, polycarbonate, cyclic olefin copolymer, or cyclic olefin polymer.

14. The light-induced fluorescence measuring device according to claim 1, wherein the second resin material has a same refractive index as the first resin material.

15. The light-induced fluorescence measuring device according to claim 4 further including a third color glass filter disposed at the aperture and configured to transmit light having a predetermined wavelength.

16. The light-induced fluorescence measuring device according to claim 1, wherein the second resin material includes a plurality of resin layers, with each of the plurality of resin layers containing the pigment.

17. The light-induced fluorescence measuring device according to claim 1 further including an electric power source embedded in the second resin material and configured to feed electric power to the solid light source and the fluorescence measuring unit.

18. The light-induced fluorescence measuring device according to claim 1, wherein the solid light source and the fluorescence measuring unit are embedded in the second resin material.

* * * * *